United States Patent [19]

Repine et al.

[11] Patent Number: 5,389,522
[45] Date of Patent: Feb. 14, 1995

[54] SERUM ANTIOXIDANTS AS PREDICTORS OF THE ADULT RESPIRATORY DISTRESS SYNDROME IN SEPTIC PATIENTS

[76] Inventors: John E. Repine, 2275 Cherry Hills Farm Dr., Englewood, Colo. 80110; Jonathan A. Leff, 5905 S. Fairfax Ct., Littleton, Colo. 80121

[21] Appl. No.: 34,935

[22] Filed: Mar. 19, 1993

[51] Int. Cl.⁶ .................... C12Q 1/26; C12Q 1/30; G01N 33/53
[52] U.S. Cl. ...................... 435/7.4; 435/27; 435/25; 435/7.9; 435/7.92; 435/7.95
[58] Field of Search .................. 435/7.4, 7.9, 7.92, 435/7.94, 7.95, 27, 25

[56] References Cited

U.S. PATENT DOCUMENTS 3,926,732  12/1975  Rosen et al. ............ 435/25
5,147,783   9/1992  Uda et al. ............. 435/7.9

OTHER PUBLICATIONS

Abbas, A. K., et al. Cellular and Molecular Immunology. Philadelphia: W. B. Saunders Co., 1991, p. 231.
Leff, J. A., et al. Increased hydrogen peroxide scavenging and catalase activity in serum from septic patients who subsequently develop the adult respiratory distress syndrome (ARDS) Am. Rev. Resp. Dis. 143:A805, 1991.
Leff, J. A. et al. Serum Catalase Activity is increased in Septic Patients and Predictive of Adult respiratory distress syndrome (ARDS) development. Clinical Research 40 (1) 67A, 1992.
Leff, J. A. et al. Serum antioxidants as predictors of adult respiratory distress syndrome in patients with sepsis, The Lancet 341: Mar. 27, 1993, pp. 777-780.
Alberts et al., "Tracing Cellular Molecules with Radioactive Isotopes and Antiobodies," *Molecular Biology of the Cell,* pp. 177-180 (Alberts et al. eds., Garland Publishing, Inc) (1989).
Allen et al., "Increased Membrane Binding of Erythrocyte Catalase in Hereditary Spherocytosis and in Metabolically Stressed Normal Cells," *Blood,* 49(1): 113-123 (Jan., 1977).
Donnelly et al., "Interleukin-8 and development of adult respiratory distress syndrome in at-risk patient groups," *Lancet,* 341:643-647 (Mar. 13, 1993).
Harlow and Lane, "Immunoassays," *Antibodies A Laboratory Manual,* pp. 578-612 (Cold Spring Harbor Laboratory) (1988).
Hensyl (ed.), *Stedman's Medical Dictionary,* 25th Edition, pp. 1404 & 1442 (Williams & Wilkins) (1990).
Knaus, "Prognostic Factors in the Intensive Care Unit with Special Emphasis on Acute Respiratory Failure," *Adult Respiratory Distress Syndrome,* pp. 91-104 (Zapol and Lemaire, eds., Marcel Dekker, Inc.) (1991).
Litwin et al., "Immunolocytochemical Localization of Peroxisomal Enzymes in Human Liver Biopsies," *American Journal of Pathology,* 128(1): 141-150 (Jul., 1987).

(List continued on next page.)

*Primary Examiner*—Esther M. Kepplinger
*Assistant Examiner*—Eve J. Wilson
*Attorney, Agent, or Firm*—Marshall, O'Toole, Gerstein, Murray & Borun

[57] ABSTRACT

At the initial diagnosis of sepsis (6-24 h before the development of ARDS), serum manganese superoxide dismutase (MnSOD) levels and catalase activities are increased in septic patients who subsequently developed ARDS compared to septic patients who did not develop ARDS. Increases in MnSOD and catalase may be used to predict the occurrence of ARDS in septic patients with the same sensitivity, specificity and efficiency as parallel assessments of serum lactate dehydrogenase (LDH) and Factor VIII levels. Evaluation of serum MnSOD and catalase as well as these other accessible markers facilitates identification of subsets of patients and allows prospective treatment of septic patients who are destined to develop ARDS.

5 Claims, 2 Drawing Sheets

OTHER PUBLICATIONS

Ogata and Mizugaki, "Single Radial Diffusion Using Catalase Antibody as Screening Method of Hypocatalasemia," *Tohoku J. exp. Med.*, 111:361–364 (1973).

Wieacker et al., "Assignment of the Gene Coding For Human Catalase to the Short Arm of Chromosome 11," *Ann. Genet.*, 23:73–77 (1980).

Wiemer et al., "Production and Characterisation of monoclonal antibodies against native and disassembled human catalase," *Journal of Immunological Methods*, 151:165–175 (1992).

Baldwin, et al., *The Lancet*, "Oxidant Activity in Expired Breath of Patients with Adult Respiratory Distress Syndrome," 1:11–14 (Jan. 4, 1986).

Bernard, et al., *Am. Rev. Respir. Dis.*, "Glutathione (GSH) Repletion by N-Acetylcysteine (NAC) in Patients with the Adult Respiratory Distress Syndrome" (ARDS, p. A221 (1989).

Beutler, *Red Cell Metabolism: A Manual of Biochemical Methods*, Grune & Stratton, Inc., pp. 1–172 (1984).

Brown, et al., PNAS, "Endotoxin pretreatment inceases endogenous myocardial catalase activity and decreases ischemia-reperfusion injury of isolated rat hearts," 86:2516–2520 (Apr., 1989).

Buhl, et al., *The Lancet*, "Systemic Glutathione Deficiency in Symptom-Free HIV-Seropositive Individuals," 2:1294–1298 (Dec. 2, 1989).

Carvalho, et al., *New England J. Med.*, "Altered Factor VIII in Acute Respiratory Failure," 307(18):1113–1119 (Oct. 28, 1982).

Cejka, et al., *Clin. Chem.*, "Enzyme Immunoassay for Factor VIII-Related Antigen," 28(6):1356–1358 (1982).

Cochran, *In; Sampling Techinques*, 2nd Ed. New York, John Wiley & Sons, Inc., "Sampling for Proportions and Percentages," pp. 54–59 (1963).

Cochrane, et al., *J. Clin. Invest.*, "Pathogenesis of the Adult Respiratory Syndrome," 71:754–761 (Mar., 1983).

Corcoran, et al., *Clin. Chem.*, "Albumin Determination by a Modified Bromcresol Green Method," 23(4): 765–766 (1977).

Duswald, et al., *Surgery*, "Released Granulocytic elastase: An indicator of pathobiochemical alterations in septicemia after abdominal surgery," 98(5):892–899 (Nov., 1985).

Fowler, et al., *Ann. Intern. Med.*, "Adult Respiratory Distress Syndrome: Risk with Common Predispositions," 98:593–597 (May, 1983).

Grum, et al., *J. Crit. Care*, "Plasma Xanthine Oxidase Activity in Patients with Adult Respiratory Distress Syndrome," 2:22–26 (Mar., 1987).

Hilgenfelt, et al., *Eur. J. Clin Pharmacol.*, "Relationship between angiotensinogen, $\alpha_1$-protease inhibitor elastase complex, antithrombin III and C-reactive protein in septic ARDS," 38:125–131 (1990).

Hyers, et al., *Am. Rev. Respir. Dis.*, "Tumor Necrosis Factor Levels in Serum and Bronchoalveolar Lavage Fluid of Patients with the Adult Respiratory Syndrome," 144:268–271 (1991).

Kawaguchi, et al., *Biochem. Biopys. Res. Comm.*, "Stimulation of Mn-Superoxide Dismutase Expression by Tumor Necrosis Factor-$\alpha$: Quantitative Determination of Mn-SOD Protein Levels in TNF-Resistant and Sensitive Cell by Elisa," 171(3) 1378–1386 (Sep. 28, 1990).

Knaus, et al., *Crit. Care Med.*, "APACHE II: A severity of disease classification system," 13(10):818–829 (Oct., 1985).

Leff, et al., *Free Radical Biol. Med.*, "Progressive Increases in Serum Catalase Activity in Advancing Human Immunodeficiency Virus Infection," 13:143–149 (1992).

Leff, et al., *Am. Rev. Respir. Dis.*, "Increased Serum Catalase Activity in Septic Patients with the Adult Respiratory Distress Syndrome," 146:985–989 (1992).

Leff, et al., *J. Appl. Physiol*, "Human serum catalase decreases endothelial cell injury from hydrogen peroxide,": 71(5):1903–1906 (Jun., 1991).

Marks, et al., *Am. Rev. Respir. Dis.*, "Plasma Tumor Necrosis Factor in Patients with Septic Shock," 141:94–97 (1990).

McGuire, et al., *J. Clin. Invest.*, "Studies on the Pathogenesis of the Adult Respiratory Distress Syndrome," 69:543–553 (Mar., 1982).

Pacht, et al., *Chest*, "Deficiency of Alveolar Fluid Glutathione in Patients with Sepsis and the Adult Respiratory Distress Syndrome," 100(5):1397–1403 (Nov., 1991).

Parsons, et al., *Am. Rev. Respir. Dis.*, "The Association of Circulating Endotoxin with the Development of the Adult Respiratory Distress Syndrome," 140:294–301 (Jan. 23, 1989).

(List continued on next page.)

OTHER PUBLICATIONS

Repine, *The Lancet,* "Scientific perspectives on adult respiratory distress syndrome," 339:466–469 (Feb. 22, 1992).

Rocker, et al., *The Lancet,* "Diagnostic Criteria for Adult Respiratory Distress Syndrome: Time for Reappraisal," 1:120–123 (Jan. 21, 1989).

Rubin et al., *J. Clin. Invest.,* "Elevated von Willebrand Factor Antigen is an Early Plasma Predictor of Acute Lung Injury in Nonpulmonary Sepsis Syndrome," 86:474–480 (Aug. 1990).

Siler, et al., *Exp. Lung Res.,* "Immunoreactive Interleukin-1 in Bronchoalveolar Lavage Fluid of High--Risk Patients and Patients with the Adult Respiratory Distress Syndrome," 15:881–894 (Mar, 1989).

Suter, et al., *Am. Rev. Resp. Dis.,* "High Bronchoalveolar Levels of Tumor Necrosis Factor and its Inhibitors, Interleukin-1, and Elastase, in Patients with the Adult Respiratory Distress Syndrome after Trauma, Shock or Sepsis," 145:1016–1022 (Oct. 28, 1992).

Taniguchi, *Adv. Clin. Chem.,* "Clinical Significances of Superoxide Dismutases: Changes in Aging, Diabetes, Ischemia and Cancer," 29:1–59 (1992).

Terada, et al., *J. Appl. Physiol.* "Hyperoxia and self–or neutrophil-generated $O_2$ metabolites inactivate xanthine oxidase," 265:2349–2353 (Sep., 1988).

Ward, et al., *J. Clin. Invest.,* "Systemic Complement Activation, Lung Injury, and Products of Lipid Peroxidation," 76:517–527 (Aug., 1985).

White, et al., *J. Appl. Physiol.,* "Cytokines increase rat lung antioxidant enzymes during exposure to hyperoxia," 66:1003–1007 (1989).

Wong, et al., *Science,* "Induction of Manganous Superoxide Dismutase by Tumor Necrosis Factor: Possible Protective Mechanism," 242:941–944 (Nov. 1988).

SERUM ANTIOXIDANTS AS PREDICTORS OF THE ADULT RESPIRATORY DISTRESS SYNDROME IN SEPTIC PATIENTS

BACKGROUND

The present application relates in general to methods and apparatus for performing assays for disease states, and in particular to methods and apparatus for performing assays for adult respiratory distress syndrome (ARDS).

ARDS is an acute inflammatory process characterized by lung neutrophil accumulation, lung edema and progressive hypoxemia [Repine, Lancet, 339, 466–469 (1992)]. ARDS occurs as a complicating factor in patients with sepsis as well as numerous other predisposing conditions. Since many common and diverse risk factors lead to the development of ARDS, but ARDS develops only relatively rarely, pretreating everyone at risk for ARDS is not practical [Fowler et al., Ann. Intern. Med., 98, 593–597 (1983)]. Because a better understanding of ARDS is emerging and various interventions which can limit inflammation are forthcoming, it has become a major goal to identify accessible and repeatable markers in at risk patients which predict the development of ARDS. This will enable experimental therapies to be prospectively and effectively evaluated in smaller, better-defined groups of patients.

SUMMARY OF THE INVENTION

The present invention provides a method for identifying septic patients for prospective treatment of adult respiratory distress syndrome including the step of determining a high (greater than an established baseline) serum level of manganese superoxide dismutase.

The present invention also provides a method for identifying septic patients for prospective treatment of adult respiratory distress syndrome including the step of determining a high (greater than an established baseline) serum level of catalase.

According to the present invention, apparatus for identifying septic patients for prospective treatment of adult respiratory distress syndrome includes means for determining a high (greater than an established baseline) serum level of manganese superoxide dismutase.

The present invention also provides apparatus for identifying septic patients for prospective treatment of adult respiratory distress syndrome including means for determining a high (greater than an established baseline) serum level of catalase.

Figure 1:
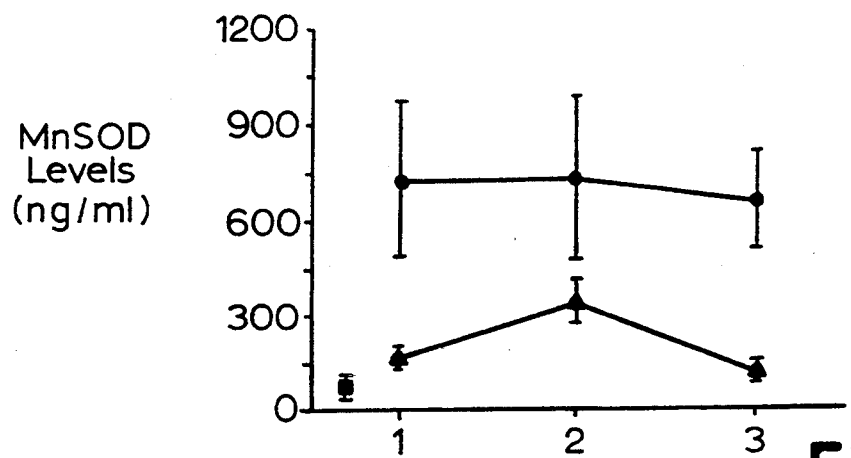
FIG. 1 is a graph of MnSOD levels for healthy control subjects (squares); and of septic patients who did not develop ARDS (triangles) and septic patients who developed ARDS (circles) at three times: at diagnosis of sepsis (1), at diagnosis of ARDS (2) and after diagnosis of ARDS (3)

In the experiments illustrated in FIGS. 1–6, septic patients were enrolled (0 h) and studied sequentially for the next 48 h. Points were plotted at the diagnosis of sepsis (0 h at 1), at the diagnosis of ARDS (6–24 h after the diagnosis of sepsis at 2) and after the diagnosis of sepsis (6–24 h after the diagnosis of ARDS at 3). Each value is the mean ± SE of 3–20 determinations.

DETAILED DESCRIPTION OF THE INVENTION

In the present investigation, three antioxidant enzymes [manganese superoxide dismutase (MnSOD), catalase and glutathione peroxidase (GPX)] were compared with three other potential markers [Factor VIII [Carvalho et al., N. Engl. J. Med., 307, 1113–1119 (1982) and Rubin et al., J. Clin. Invest., 86, 474–480 (1990)] LDH [Ward et al., J. Clin. Invest. 76, 517–527 (1985) and Dwenger et al., In: Sturm, ed. Adult Respiratory Distress Syndrome, Berlin Heidelberg: Springer-Verlag, 91–127 (1991)]] and $\alpha_1$Pi-elastase complexes [Rocker et al., Lancet, 1, 120–123 (1989) and Hilgenfeldt et al., Eur. J. Clin. Pharmacol, 38, 125–131 (1990)] for their ability to predict the development of ARDS in patients with sepsis.

Alterations occur in the oxidantantioxidant balance in ARDS and in other disease states that appear to involve oxygen radicals in their pathogenesis [Leff et al., Free Radical Biol. Med., 13, 143–149 (1992); Leff et al., Am. Rev. Respir. Dis, 146, 985–989 (1992); Buhl et al., Lancet, 2, 1294–1298 (1989); Bernard et al., Am. Rev. Resp. Dis., 139, A221 (Abstract) (1989); and Pacht et al., Chest, 100, 1397–1403 (1991)]. In addition, patients with established ARDS have elevated serum catalase activity [Leff et al., Am. Rev. Respir. Dis, 146, 985–989 (1992)]. Serum catalase activity increased in a rat model of burn-induced acute lung injury [Leff et al., Inflammation (In Press) (1992)].

EXAMPLE

Patient Consent and Selection.

After written consent was obtained from the patient or a family member, each subject was studied using a protocol which was approved by an institutional human subjects review committee. All patients (n=26) who were identified within 8 h of the diagnosis of sepsis were eligible for enrollment. Patients with sepsis had a serious bacterial infection and either (a) a rectal or core temperature exceeding 39° C. or (b) a peripheral leukocyte count of >12,000 cells/mm³ or >20% immature neutrophils. Septic patients also had at least one of the following: a positive blood culture involving a commonly accepted pathogen, a strongly suspected or proven source of systemic infection, gross pus in a closed space, unexplained systemic arterial hypotension (systolic blood pressure less than 80 mm Hg), systemic vascular resistance less than 800 dyn×s×cm² and/or unexplained metabolic acidosis [Parsons et al., Am. Rev. Resp. Dis., 140, 294–301 (1989)].

Patients with ARDS (n=6) met the following criteria: (1) acute respiratory failure requiring mechanical ventilation, (2) bilateral pulmonary infiltrates, (3) pulmonary capillary wedge pressure <18 mm Hg, (4) static pulmonary compliance <50 ml/cm H₂O, and (5) arterial to alveolar partial pressure of oxygen ratio of <0.25 [Parsons et al., Am. Rev. Resp. Dis., 140, 294–301 (1989)]. Serum and plasma samples were obtained at the diagnosis of sepsis (0 h) and at the diagnosis of ARDS (6–24 h after the diagnosis of sepsis) and after the diagnosis of ARDS (6–24 h after the diagnosis of ARDS) either through an indwelling arterial or venous catheter or by direct venipuncture. Patients were divided into two groups: septic patients who did not develop ARDS and septic patients who later developed ARDS. Patients were prospectively and sequentially studied until death or discharge. All assays were performed by personnel who were unaware of the diagnoses. Control subjects (n=15) were healthy individuals.

Source of reagents.

Hanks' balanced salt solution (HBSS) was purchased from Gibco Laboratories (Grand Island, N.Y.). All other reagents were obtained from Sigma Chemical Company (St. Louis, Mo.).

Measurement of serum markers.

MnSOD [Kawaguchi et al., Biochem. Biophys. Res. Commun. 171, 1378–1386 (1990)], Factor VIII antigen [Cejka, Clin. Chem., 28(6), 1356–1358 (1982)] and $\alpha_1$Pi-elastase complexes [Duswald et al., Surgery, 98, 892–899 (1985)] were measured by ELISA. Catalase was assessed by polarographic assessment of $O_2$ evolution [Leff et al., J. Appl. Physiol., 71(5), 1903–1906 (1991)]. GPX was measured as the oxidation of NADPH at 340 nm in glutathione reductase, glutathione and t-butyl hydroperoxide [Beutler, A Manual of Biochemical Methods, Orlando, Grune & Stratton, Inc., 1–172 (1984)], LDH [Beutler, A Manual of Biochemical Methods, Orlando, Grune & Stratton, Inc., 1–172 (1984)] and albumin [Corcoran et al., Clin. Chem., 23, 765–766 (1977)] were assayed spectrophotometrically. Uric acid was measured by HPLC [Terada et al., J. Appl. Physiol., 65, 2349–2353 (1988)].

Statistical analyses.

Patient groups were compared using an analysis of variance with a Student-Newman-Keuls test of multiple comparisons. An unpaired t test was used to compare the clinical characteristics of septic patients with or without ARDS. For calculations of sensitivity, specificity, positive or negative predictive values and efficiency, 95% confidence intervals were determined based on the binomial distribution [Cochran, In: Sampling Techniques, 2nd ed., New York, John Wiley & Sons, Inc., 54–59 (1963)]. Significance was accepted at a p value of <0.05.

Clinical Parameters.

Septic patients who subsequently developed ARDS and septic patients who did not develop ARDS were the same (p>0.05) with respect to age, gender, hematocrit, hemoglobin, blood leukocyte count, blood neutrophil count, serum SGOT, bilirubin, albumin, uric acid levels and APACHE II score [Leff et al., Ann. Rev. Respir. Dis., 146, 985–989 (1992); Knaus et al., Crit. Care Med., 13, 818–289 (1985)]. The mortality of septic patients who developed ARDS was 50% (3 of 6) compared to a mortality of 30% (6 of 20) in septic patients who did not develop ARDS.

Blood markers patterns.

Septic patients had increased (p<0.05) serum MnSOD levels compared to control subjects (FIG. 1). However, at the initial diagnosis of sepsis (approximately 6–24 h before diagnosis of ARDS), septic patients who eventually developed ARDS had increased (p<0.05) serum MnSOD levels compared to septic patients who did not develop ARDS. Serum MnSOD levels remained elevated for the next 48 h in patients who developed ARDS while MnSOD levels returned to control levels during the next 48 h in septic patients who did not develop ARDS.

Figure 2:
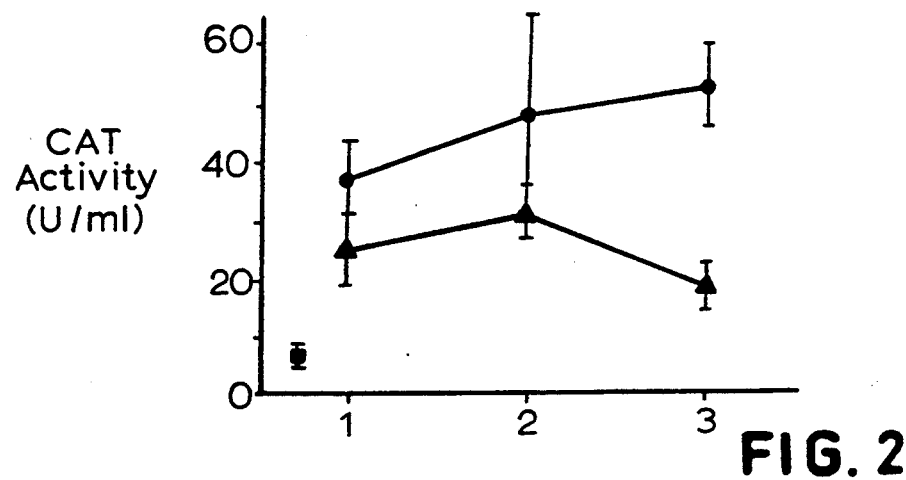
FIG. 2 is a graph of CAT activity for healthy control subjects (squares); and of septic patients who did not develop ARDS (triangles) and septic patients who developed ARDS (circles) at three times: at diagnosis of sepsis (1), at diagnosis of ARDS (2) and after diagnosis of ARDS (3)

Similarly, at the diagnosis of sepsis, serum from septic patients had more (p<0.05) catalase activity than serum from control subjects. Again, at the initial diagnosis of sepsis, patients who later developed ARDS had more (p<0.05) serum catalase activity than septic patients who did not develop ARDS (FIG. 2). During the next 48 h, serum catalase activity increased progressively in septic patients who developed ARDS but did not change in septic patients who did not develop ARDS.

Figure 3:
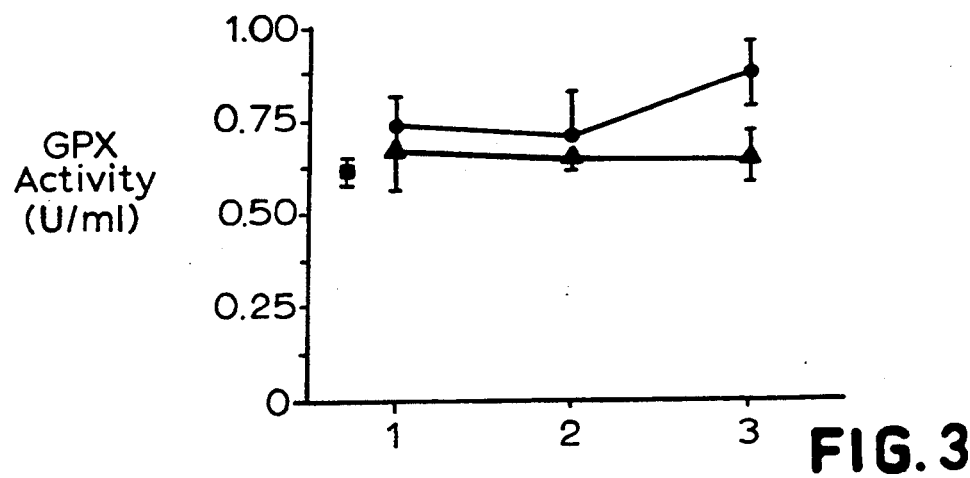
FIG. 3 is a graph of GPX activity for healthy control subjects (squares); and of septic patients who did not develop ARDS (triangles) and septic patients who developed ARDS (circles) at three times: at diagnosis of sepsis (1), at diagnosis of ARDS (2) and after diagnosis of ARDS (3)

In contrast to MnSOD levels and catalase activities, serum GPX activity was essentially the same (p>0.05) in control subjects and septic patients regardless of whether ARDS ensued (FIG. 3).

Figure 4:
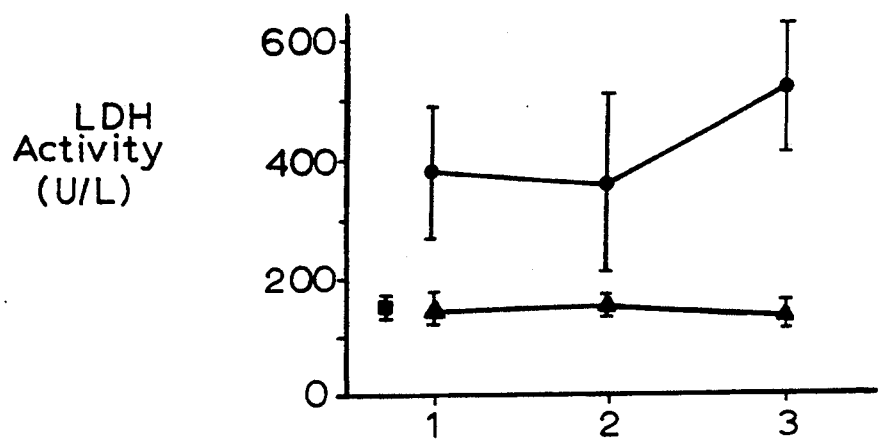
FIG. 4 is a graph of LDH activity for healthy control subjects (squares); and of septic patients who did not develop ARDS (triangles) and septic patients who developed ARDS (circles) at three times: at diagnosis of sepsis (1), at diagnosis of ARDS (2) and after diagnosis of ARDS (3)
Figure 5:
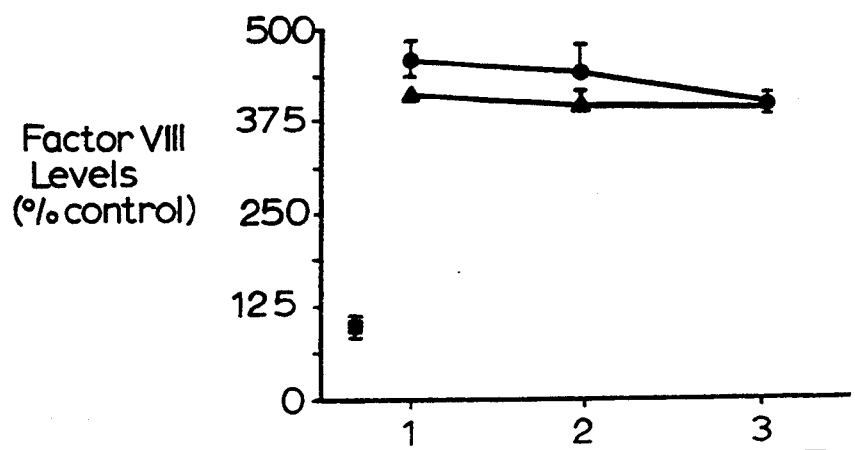
FIG. 5 is a graph of Factor VIII levels for healthy control subjects (squares); and of septic patients who did not develop ARDS (triangles) and septic patients who developed ARDS (circles) at three times: at diagnosis of sepsis (1), at diagnosis of ARDS (2) and after diagnosis of ARDS (3)

Serum from septic patients who subsequently developed ARDS also had increased (p<0.05) LDH activity compared to serum from septic patients who did not develop ARDS. Serum from septic patients who did not develop ARDS had the same (p>0.05) LDH activity as serum from control subjects (FIG. 4). Serum LDH measurements increased during the 48 h study period in septic patients who developed ARDS but not in septic patients who did not develop ARDS.

Septic patients who did or did not develop ARDS (FIG. 5) had similarly increased (p<0.05) serum Factor VIII levels compared to control subjects. Septic patients who did and did not develop ARDS had similar (p>0.05) Factor VIII levels.

Figure 6:
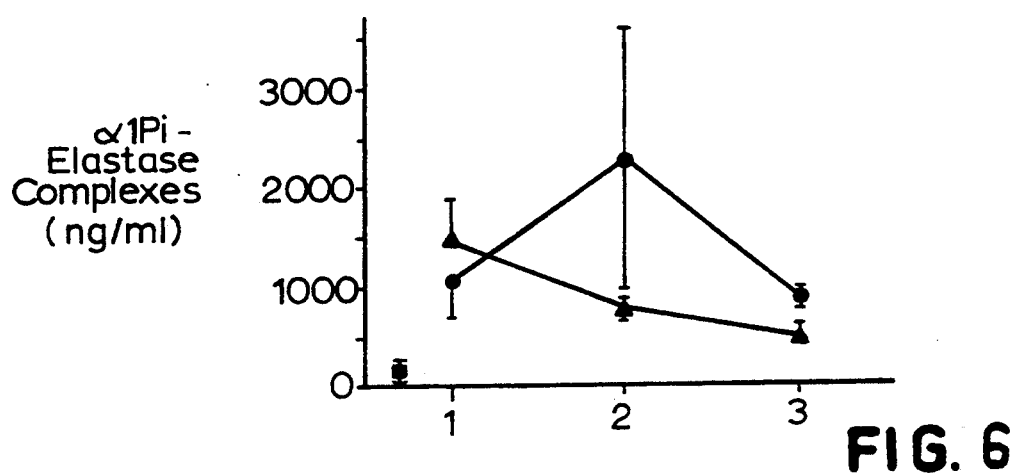
FIG. 6 is a graph of levels of $\alpha_1$Pi-elastase complexes for healthy control subjects (squares); and of septic patients who did not develop ARDS (triangles) and septic patients who developed ARDS (circles) at three times: at diagnosis of sepsis (1), at diagnosis of ARDS (2) and after diagnosis of ARDS (3).

Finally, plasma $\alpha_1$Pi-elastase complexes were increased in all septic patients at the initial diagnosis of sepsis but differences between septic patients who did or did not develop ARDS were manifest only at the time of diagnosis of ARDS (6–24 h after the diagnosis of sepsis) (FIG. 6). By 48 h after the initial diagnosis of sepsis, $\alpha_1$Pi-elastase complexes had similarly decreased in septic patients independent of the development of ARDS.

Analyses of serum markers.

First, no correlations were found at any time between any of the six markers; Second, the positive and negative predictive values and the sensitivity and specificity of Serum MnSOD levels ($\geq$450 ng/ml), catalase activity ($\geq$30 U/ml), LDH activity $\geq$250 U/L and Factor VIII levels $\geq$445% control were comparable in predicting the development of ARDS in septic patients (Table 1). Third, serum MnSOD levels, catalase and LDH activity exceeded 450 ng/ml, 30 U/ml and 250 U/L, respectively, approximately 9 h, 12 h and 12 h, on average, respectively, before the diagnosis of ARDS. Further results appear in Table 1.

TABLE 1

Comparison of the Sensitivity and Specificity of Blood Markers as Predictors of ARDS in Septic Patients

| Parameter | Sensitivity | Specificity | Positive Predictive Value | Negative Predictive Value | Efficiency |
|---|---|---|---|---|---|
| MnSOD ≧450 ng/ml | 67% (42–94) | 88% (75–98) | 67% (4–94) | 88% (75–98) | 83% (70–94) |
| Catalase ≧30 U/ml | 83% (61–99) | 65% (49–82) | 42% (25–68) | 93% (81–100) | 69% (55–84) |
| GPX ≧0.72 U/ml | 50% (27–85) | 47% (31–69) | 25% (12–53) | 73% (53–92) | 48% (34–66) |
| LDH ≧250 U/L | 67% (42–94) | 78% (62–92) | 50% (29–81) | 88% (74–98) | 75% (61–89) |
| Factor VIII ≧445% Control | 83% (61–99) | 67% (42–94) | 45% (27–73) | 92% (80–100) | 71% (57–85) |
| $\alpha_1$Pi-elastase >940 ng/ml | 67% (37–98) | 64% (50–80) | 18% (8–47) | 94% (84–100) | 64% (51–79) |

In Table 1 each value represents 3–20 determinations at study entry (t=0 h). Values in parentheses represent 95% confidence intervals. Also in Table 1; Sensitivity=TP/TP+FN; Specificity=TN/TN+FP; Positive Predictive Value=TP/TP+FP; Negative Predictive Value=TN/TN+FN; and Efficiency=TP+TN/TP+FP+TN+FN.

In Table 1, results are shown for six sequentially measured factors in the blood of septic patients who were predisposed to develop ARDS. Nine to twelve hours before the development of ARDS, two serum antioxidant enzymes, MnSOD and catalase, were increased in septic patients who later developed ARDS compared to septic patients who did not develop ARDS and that both of these factors predicted the development of ARDS in septic patients with as good a sensitivity, specificity and efficiency as measurements of LDH and Factor VIII. By comparison, measurements of GPX and $\alpha_1$Pi-elastase complexes were neither different in septic patients who did or did not subsequently develop ARDS nor effective in predicting the development of ARDS in septic patients.

Assessment of MnSOD and catalase are useful for defining the pathogenesis of ARDS or identifying patients with similar pathophysiologies. Each measurement is accessible, repeatable and relatively easy to perform. Based on assessment of these markers, study of prophylactic treatment is facilitated by reducing the number of at risk individuals who need to be studied to obtain patients with ARDS.

Increases in serum MnSOD levels and serum catalase activity may also have functional importance. MnSOD and catalase may diminish oxidant insults mediated by superoxide anion($O_2-$.) or hydrogen peroxide ($H_2O_2$) or their products such as hydroxyl radical (.OH). This possibility may be especially relevant because accelerated intravascular generation of oxygen radicals from stimulated neutrophils, circulating xanthine oxidase or other sources are implicated in the pathogenesis of sepsis and ARDS [McGuire et al., J. Clin. Invest., 69, 543–553 (1982); Cochrane et al., J. Clin. Invest. 71, 754–758; (1983); Baldwin et al., Lancet, 1, 11–14 (1986) and Grum et al., J. Crit. Care, 2, 22–26 (1987)].

Because the patterns were different for various markers and no two markers correlated with each other, each factor may represent a distinct process and these factors may more correctly reflect various processes occurring in septic patients with ARDS rather than ARDS per se. The present work has focused on sepsis-induced ARDS, so different mechanisms may be present in patients who develop ARDS following trauma and other predispositions.

The origins of the factors, although unclear, most likely are multiple. Lung tissue injury is a possible source for increases in LDH, MnSOD, catalase and Factor VIII levels. Endothelial cells are rich in these factors and, if perturbed, may readily increase the levels of these factors in the blood. However, intravascular neutrophil activation may be responsible for increases in $\alpha_1$Pi-elastase complexes because elastase may be present only in neutrophils. Notably, increases in $\alpha_1$Pi-elastase complexes occurred relatively later, at the diagnosis of ARDS, and then decreased by 48 h after the diagnosis of sepsis, which may indicate a decline in neutrophil activity. Red blood cell (RBC) hemolysis may be a source for increases in serum catalase and LDH activity, but not MnSOD or Factor VIII levels may not, because RBCs do not contain the latter. Serum catalase activity is also increased in the serum of rats subjected to skin burn [Leff et al., Inflammation (In Press) (1992)], and patients with the acquired immunodeficiency syndrome [Leff et al., Am. Rev. Respir. Dis, 146, 985–989 (1992)], but again, in these situations, the source is unclear. Elevations of IL-1, tumor necrosis factor (TNF) and endotoxin have been found in ARDS patients [Parsons et al., Am. Rev. Resp. Dis., 140, 294–301 (1989); Suter et al., Am. Rev. Resp. Dis., 145, 1016–1022 (1992); Siler et al., Exp. Lung Res., 15(6), 881–894 (1989); Hyers et al., Am. Rev. Respir. Dis., 144, 268–271 (1991) and Marks et al., Am. Rev. Resp. Dis., 141, 94–97 (1990)] and may cause increases in antioxidants such as MnSOD and catalase [White et al., J. Appl. Physiol., 66, 1003–1007 (1989); Wong et al., Science, 242, 941–944 (1988); Brown et al., Proc. Natl. Acad. Sci. (USA), 86, 2516–2520 (1989) and Taniguchi, Adv. Clin. Chem., 29, 1–59 (1992)].

Although the present invention is illustrated by the above embodiments, it is expected that variations and modifications will occur to those skilled in the art upon consideration of the present disclosure. Accordingly, it is intended that the present invention include all modifications and variations which come within the scope of the claims.

What is claimed is:

1. A method for predicting the development of adult respiratory distress syndrome in a septic patient comprising the steps of providing serum of said patient, determining said patient's serum level of manganese superoxide dismutase, comparing said patient's serum level of manganese superoxide dismutase to an established baseline serum level of manganese superoxide dismutase, a serum level greater than or equal to said baseline serum level being predictive of the development of ARDS, and diagnosing ARDS development potential if said patient's serum level of manganese superoxide dismutase is greater than or equal to said established baseline serum level of manganese superoxide dismutase.

2. The method of claim 1 wherein the patient's serum level of manganese superoxide dismutase is determined by ELISA.

3. The method of claim 1 wherein said established baseline serum level of manganese superoxide dismutase is 450 ng/ml.

4. The method of claim 1 further comprising the steps of determining said patient's serum level of catalase activity, comparing said patient's serum level of catalase activity to an established baseline serum level of catalase activity, a serum level greater than or equal to said baseline serum level of catalase activity being predictive of the development of ARDS, and diagnosing ARDS development potential if said patient's serum level of catalase is greater than or equal to said established baseline serum level of catalase.

5. The method of claim 4 wherein said established baseline serum level of catalase activity is 30 U/ml.

* * * * *

UNITED STATES PATENT AND TRADEMARK OFFICE
CERTIFICATE OF CORRECTION

PATENT NO.   :   5,389,522

DATED        :   February 14, 1995

INVENTOR(S)  :   Repine et al.

It is certified that error appears in the above-identified patent and that said Letters Patent is hereby corrected as shown below:

At col. 1, line 5, insert --This invention was made with Government support under contracts HL 01849, HL 40784, and HL 45582 awarded by the National Institutes of Health. The Government has certain rights in this invention.--

Signed and Sealed this

Seventh Day of May, 1996

Attest:

BRUCE LEHMAN

Attesting Officer        Commissioner of Patents and Trademarks